United States Patent [19]
Siochi et al.

[11] Patent Number: 5,724,403
[45] Date of Patent: *Mar. 3, 1998

[54] VIRTUAL COMPENSATOR

[75] Inventors: Ramon Alfredo Carvalho Siochi, Fairfield; Francisco Miguel Hernandez-Guerra, Concord, both of Calif.

[73] Assignee: Siemens Medical Systems, Inc., Iselin, N.J.

[*] Notice: The term of this patent shall not extend beyond the expiration date of Pat. No. 5,563,925.

[21] Appl. No.: 671,914

[22] Filed: Jun. 28, 1996

Related U.S. Application Data

[63] Continuation-in-part of Ser. No. 504,937, Jul. 20, 1995, Pat. No. 5,563,925.
[51] Int. Cl.⁶ ........................................... G21F 5/04
[52] U.S. Cl. ........................... 378/150; 378/65; 250/492.1
[58] Field of Search ......................... 378/150, 65, 108, 378/145, 147, 151, 152, 156, 159; 250/492.1, 492.3, 585.1

[56] References Cited

U.S. PATENT DOCUMENTS

| | | | |
|---|---|---|---|
| 5,148,032 | 9/1992 | Hernandez | 250/492.1 |
| 5,216,255 | 6/1993 | Weidlich | 378/150 X |
| 5,351,280 | 9/1994 | Swerdloff et al. | 378/150 X |
| 5,528,651 | 6/1996 | Leskell et al. | 378/65 |
| 5,563,925 | 10/1996 | Hernandez | 378/150 |

OTHER PUBLICATIONS

Faiz M. Khan, Ph.D., "The Physics of Radiation Therapy", 2d ed., pp. 200–206.

Siemens Product Brochure, "Digital Systems for Radiation Oncology", pp. 1–16.

Martin B. Levene, M.D., et al., "Computer-Controlled Radiation Therapy", pp. 769–775, Dec. 1978.

Peter K. Kijewski et al., "Wedge-Shaped Dose Distributions by Computer-Controlled Collimator Motion", pp. 426–429, vol. 5, No. 5, Sep./Oct. 1978.

Lee M. Chin et al., "Dose Optimization With Computer-Controlled Gantry Rotation, Collimator Motion and Dose-Rate Variation", pp. 723–729, vol. 9, Dec. 1982.

*Primary Examiner*—David P. Porta
*Attorney, Agent, or Firm*—Heather S. Vance

[57] ABSTRACT

In a radiation emitting device, particularly in a radiation treatment device (2), the actual radiation delivered to an object (13) via a radiation beam (1) is adjusted to match the field to be irradiated on object (13). Jaws (250, 252, 254, 256) are arranged between a radiation source and an object (13) to provide an opening (110). The field is divided up into sections, and wedge corrections and/or monotonic functions are calculated for each of the sections. The wedge corrections and/or monotonic functions are used to deliver radiation to each of the sections in the field. Jaws (250, 252, 254, 256) and the radiation dose are controlled during the treatment of each of the sections.

25 Claims, 6 Drawing Sheets

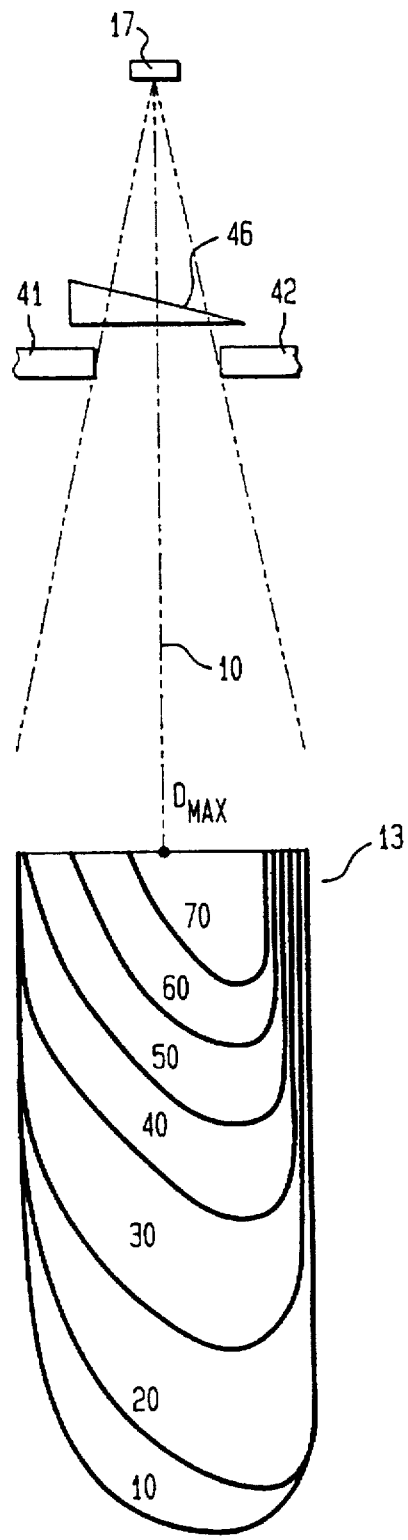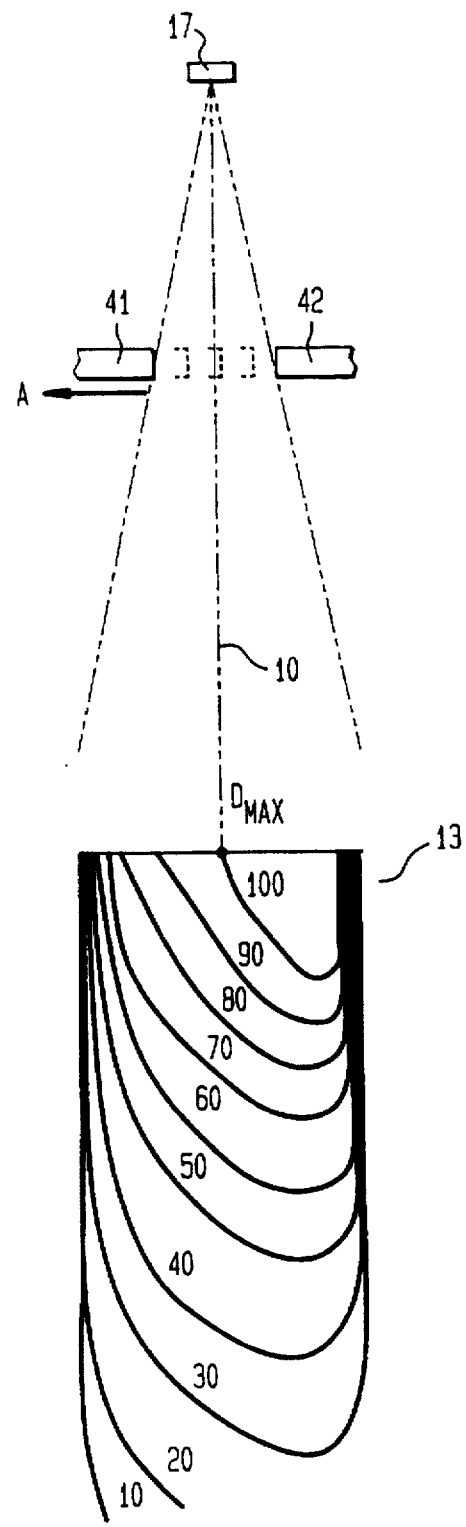
FIG. 3 (PRIOR ART)
FIG. 4

5,724,403

1

VIRTUAL COMPENSATOR

CROSS REFERENCE TO RELATED APPLICATION

This application is a continuation-in-part of U.S. patent application Ser. No. 08/504,937, filed Jul. 20, 1995 now U.S. Pat. No. 5,563,925, which is incorporated herein by reference in its entirety for all purposes.

BACKGROUND OF THE INVENTION

1. Field of the Invention

The invention relates to a radiation emitting device, and more particularly to a system and a method for adjusting the radiation delivered to an object in a radiation treatment device.

2. Description of the Related Art

Radiation-emitting devices are generally known and used, for instance, as radiation therapy devices for the treatment of patients. A radiation therapy device usually comprises a gantry which can be swiveled around a horizontal axis of rotation in the course of a therapeutic treatment. A linear accelerator is located in the gantry for generating a high-energy radiation beam for therapy. This high energy radiation beam can be an electron radiation or photon (X-ray) beam. During treatment, this radiation beam is trained on a zone of a patient lying in the isocenter of the gantry rotation.

To control the radiation emitted toward an object, a beam-shielding device such as a plate arrangement and/or collimator is usually provided in the trajectory of the radiation beam between the radiation source and the object. An example of a plate arrangement is a set of four jaws which can be used to define an opening for the radiation beam. The beam-shielding device defines a field on the object to which a prescribed amount of radiation is to be delivered.

The radiation delivered to an object may be analyzed into primary and scattered components. The primary radiation is made up of the initial or original photons emitted from the radiation source, and the scattered radiation is the result of the photons scattered by the plate arrangement itself. The beam's radiation output in free space increases because of the increased plate/collimator scatter, which is added to the primary beam. In other words, a point in the field is subjected not only to direct radiation (which is the primary component), but also to radiation that is scattered from the plate arrangement. The ratio of the radiation output in air with the scatterer to the radiation output without the scatterer for a reference field (for instance 10 cm×10 cm) is commonly called the "output factor" or the "collimator scatter factor." The concept and definition of the output factor are well understood in the art.

Thus, due to these scattered photons, the dose rate applied to the surface of the object changes dependent on the size of the opening in the plate arrangement, that is, on the field size. This means that the radiation emitted to the same spot, for instance in the center of the radiation beam onto the object, changes according to the size of the opening in the plate arrangement. When the plate arrangement shows only a small opening, then the accumulated dose at the same spot is less than the accumulated dose at the same spot when the opening is big.

Frequently, special filters or absorbing blocks are located in the trajectory of the radiation beam to modify its isodose distribution. A most commonly used filter is the wedge filter. This is a wedge-shaped absorbing block which causes a progressive decrease in the intensity across the beam, resulting in isodose curves that are modified relative to their normal positions. Such wedge filters are usually made of dense material, such as lead or steel, or other absorbing material.

The presence of a wedge filter decreases the output of the radiation-emitting device, and this decrease must be taken into account in treatment calculations. This effect is characterized as a "wedge factor." A wedge factor is defined as the ratio of doses with and without the wedge at a point in the object along the central axis of the radiation beam. The wedge factor depends on the material, size and angle of the wedge. Wedges, and in particular the wedge factor, are described in Faiz M. Khan, Ph.D, "The Physics of Radiation Therapy", Williams & Wilkins, pages 234 to 238.

The delivery of radiation by such a radiation therapy device is prescribed and approved by an oncologist. Actual operation of the radiation equipment, however, is normally done by a therapist. When the therapist administers the actual delivery of the radiation treatment as prescribed by the oncologist, the device is programmed to deliver that specific treatment. When programming the treatment, the therapist has to take into consideration the output factor and has to adjust the dose delivery based on the plate arrangement opening to achieve the prescribed radiation output on the surface of the object. This adjustment can be made according to known calculations, but the therapist normally has to do them manually, which can lead to errors. In the context of radiation therapy, a miscalculation can lead to either a dose that is too low and is ineffective, or that is too high and dangerous; a large error (e.g., a misplaced decimal point) can be lethal.

U.S. Pat. No. 5,148,032 discloses a radiation treatment device in which isodose curves in the object are adjusted both by a plate arrangement, which includes at least one movable plate that is controlled during irradiation, and by varying the radiation output of the radiation beam during irradiation, so that a wide range of variations in the possible isodose curves is obtained. A wedge-shaped isodose distribution is established, for example, by moving one plate at a constant speed while simultaneously changing the radiation output of the radiation beam. In this radiation treatment device there is no physical absorbing block in the trajectory of the radiation beam, and the therapist has to take this into account.

What is needed is a method, and corresponding system, for adjusting the delivery of radiation to the object to make sure that the actually delivered radiation output is exactly the same as the desired radiation output, independent of the use of a wedge function.

SUMMARY OF THE INVENTION

According to the invention, radiation output delivered to an object from a radiation source is adjusted. A field to be irradiated is first defined. The field is located on an object. A radiation beam is generated. The radiation beam has a variable radiation output and a substantially lossless beam path from a radiation source to the object. An opening between the radiation source and the object is defined. This opening has multiple available parameters and is capable of delimiting the radiation beam to any one of the multiple available parameters. The field is divided into multiple sections with defined parameters. Wedge corrections for each of the multiple sections are calculated. The wedge corrections are then used to treat each of the sections with radiation.

BRIEF DESCRIPTION OF THE DRAWINGS

FIG. 3 shows isodose curves for a conventional wedge filter built of an absorption block in the path of a radiation beam;

FIG. 4 shows isodose curves for an arrangement in which a wedge filter is realized by the movement of one plate of a plate arrangement in the path of the radiation beam and by changing the radiation output of the radiation beam;

DETAILED DESCRIPTION

The invention is described below with primary reference to a system for delivering X-ray radiation to a field on a patient, and for delimiting the field using at least one movable plate or jaw in the beam path from a radiation source. The invention may be used to adjust the delivery of any type of energy, for example, electrons (instead of X-rays), to any type of object (not just a human patient), provided the amount of energy delivered to the field can be sensed or estimated.

Figure 1:
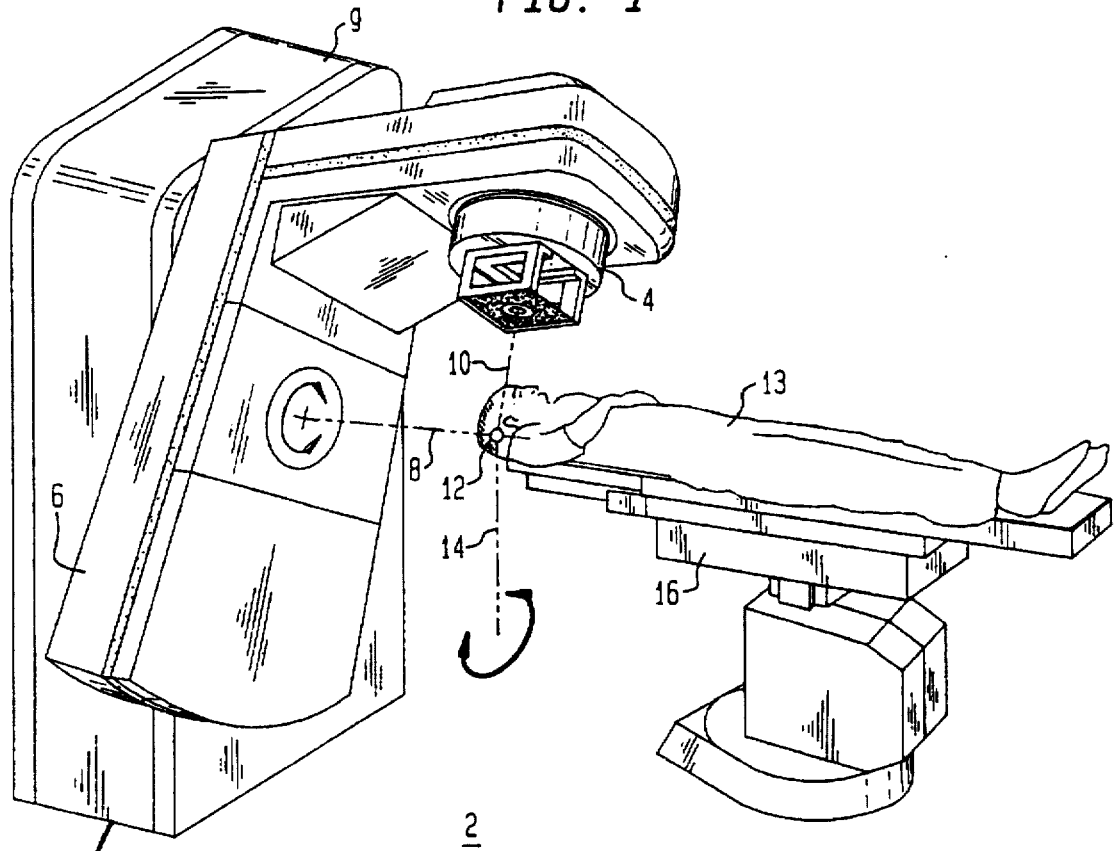
FIG. 1 shows a schematic diagram of a radiation treatment device including a treatment console constructed in accordance with the present invention.
Figure 1:
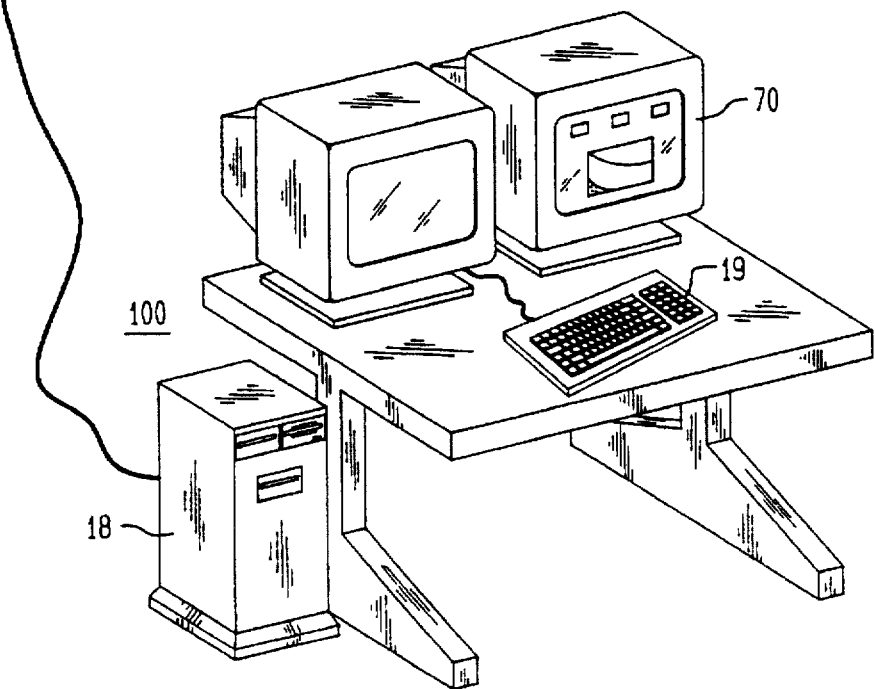

FIG. 1 shows a radiation treatment device 2 of common design, in which plates 4, a control unit in a housing 9 and a treatment unit 100 constructed in accordance with the principles of the invention are used. The radiation treatment device 2 comprises a gantry 6 which can be swiveled around a horizontal axis of rotation 8 in the course of a therapeutic treatment. Plates 4 are fastened to a projection of gantry 6. To generate the high-powered radiation required for the therapy, a linear accelerator is located in gantry 6. The axis of the radiation bundle emitted from the linear accelerator and gantry 6 is designated by 10. Electron, photon, or any other detectable radiation can be used for the therapy. During the treatment, the radiation beam is trained on a zone 12 of an object 13 (e.g., a patient who is to be treated, and who lies at the isocenter of the gantry rotation). Rotational axis 8 of gantry 6, rotational axis 14 of the area on the object to be treated, and beam axis 10 all preferably intersect in the isocenter.

The area of the patient that is irradiated is known as the field. Plates 4 are substantially impervious to the emitted radiation. They are mounted between the radiation source and the patient to delimit the field. Areas of the body (e.g., healthy tissue) are therefore subjected to as little radiation as possible, and preferably to none at all. In the preferred embodiment of the invention, at least one of the plates is movable so that the distribution of radiation over the field need not be uniform (one region can be given a higher dose than another); furthermore, the gantry can preferably be rotated so as to allow different beam angles and radiation distributions without having to move the patient around. Neither or these features is necessary according to the invention: the invention may also be used with fixed-field devices (no movable plates), with constant radiation delivery rates, and with fixed-angle beams (no rotatable gantry).

Radiation treatment device 2 also includes a central treatment processing or control unit 100, which is usually located apart from radiation treatment device 2. The radiation treatment device 2 is normally located in a different room to protect the therapist from radiation. Treatment unit 100 includes output devices, such as at least one visual display unit or monitor 70, and an input device, such as a keyboard 19. Data can also be input through data carriers, such as data storage devices, or a verification and recording or automatic set-up system 102, which is described below. The treatment processing unit 100 is typically operated by the therapist who administers actual delivery of a radiation treatment as prescribed by an oncologist. By utilizing the keyboard 19, or other input device, the therapist enters into a control unit 76 of the treatment unit 100 the data that defines the radiation to be delivered to the patient (e.g., according to the prescription of the oncologist). The program can also be input via another input device like a data storage device, through data transmission, or using the automatic set-up system 102. On the screen of a monitor 70, various data can be displayed before and during the treatment.

Figure 2:
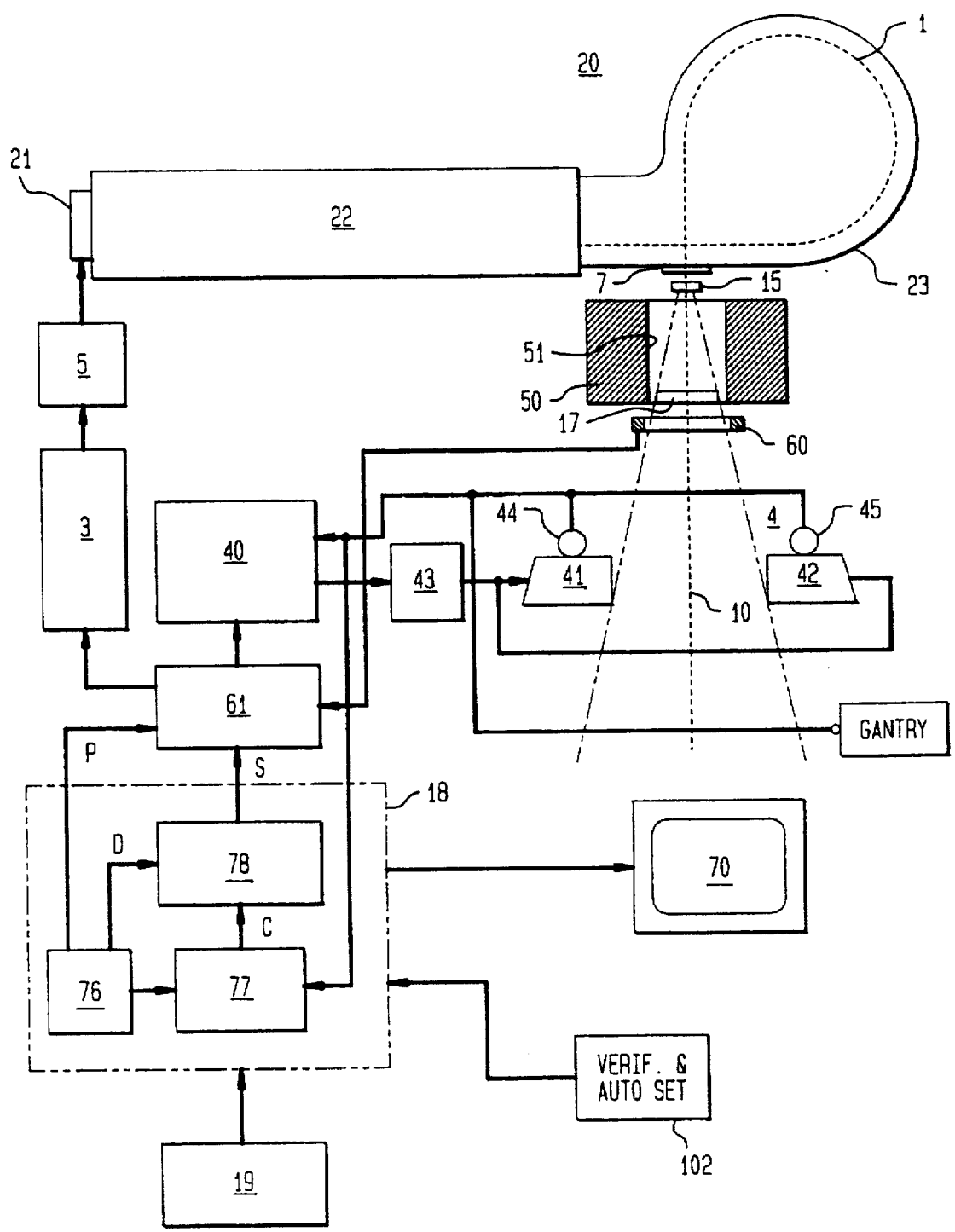
FIG. 2 is a block diagram illustrating portions of a processing unit, a control unit and a beam generation system in the radiation treatment device of FIG. 1.

FIG. 2 shows portions of an illustrative radiation treatment device 2 and portions of treatment unit 100 in more detail. An electron beam 1 is generated in an electron accelerator 20. Accelerator 20 comprises an electron gun 21, a wave guide 22 and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters a guide magnet 23, and from there is guided through a window 7 along axis 10. After passing through a first scattering foil 15, the beam goes through a passageway 51 of a shield block 50 and encounters a second scattering foil 17. Next, it is sent through a measuring chamber 60, in which the dose is ascertained. If the radiation beam is an X-ray beam, the scattering foils are replaced by a target and a flattening filter. Finally, aperture plate arrangement 4 is provided in the path of radiation beam 1, by which the irradiated field of the subject of investigation is determined. Aperture plate arrangement 4 includes a pair of plates 41 and 42. As is described above, this is just one example of a beam-shielding arrangement that can be used in the invention. The invention will work with others also as long as there is an aperture plate arrangement that defines an irradiated field.

Plate arrangement 4 comprises a pair of aperture plates 41 and 42 and an additional pair of aperture plates (not shown) arranged perpendicular to plates 41 and 42. To change the size of the irradiated field, each of the aperture plates can be moved with respect to axis 10 by a drive unit 43 which is indicated in FIG. 2 only with respect to plate 41. Drive unit 43 comprises an electric motor which is coupled to plates 41 and 42 and which is controlled by a motor controller 40. Position sensors 44 and 45 are also coupled to plates 41 and 42, respectively, for sensing their positions. This is just one example of such a system. The invention will work with other systems also, as long as there is a beam-shielding arrangement that defines an irradiated field and as long as sensors are provided to indicate the field size. For example, the plates can be replaced with a collimator containing many (e.g., 60) radiation blocking leaves.

Motor controller 40 is coupled to a dose control unit 61 which includes a dosimetry controller and which is coupled to a central processing unit 18 for providing set values for the radiation beam for achieving given isodose curves. The output of the radiation beam is measured by a measuring chamber 60. In response to the deviation between the set values and the actual values, dose control unit 61 supplies signals to trigger system 3, which changes the pulse repetition frequency so that the deviation between the set values and the actual values of the radiation beam output is minimized.

In such a radiation treatment device, the dose absorbed by object 13 is dependent on the type of filter used for shaping the radiation beam. If a wedge filter built from absorbing material is inserted in the trajectory of the radiation beam, then the preset dose has to be increased according to the wedge factor to supply the desired dose to object 13.

FIG. 3 shows isodose curves for a conventional wedge filter 46 in the path of the radiation beam emitted from radiation source 17 to object 13. The radiation beam is shaped on the one hand by the wedge filter and on the other hand by aperture plates 41 and 42. Due to the absorbing material of wedge filter 46, the isodose curve in the center 10 of the beam on object 13 has a maximum value of Dmax, which is the maximum value at a spot in center 10 of the beam on the surface of object 13 without wedge filter 46. In the illustrated example, Dmax is roughly 72%. The wedge factor defined as the ratio of doses with and without wedge filter 46 is thus, in this case 0.72.

In a first embodiment of the present invention, a wedge-shaped absorber is simulated. FIG. 4 shows isodose curves in a radiation treatment device according to the invention. Instead of including a wedge-shaped absorber in the path of the radiation beam, the filter function is performed by changing the radiation output of the radiation beam and by simultaneously moving at least one plate 41 and keeping the other plates of plate arrangement 4 stationary. A radiation treatment device having such a filter arrangement is disclosed in U.S. Pat. No. 5,148,032. Although this U.S. patent describes the possibility of moving any plate, in the following, the invention is described in connection with only one plate being moved and the other plates being kept stationary. This is for the sake of simplicity only. The invention may be used for multiple moving plates as well.

When in FIG. 4 plate 41 moves in the direction of arrow A toward plate 42 and at the same time the radiation output is changed according to a desired wedge angle, by adjusting the speed of plate 41 and/or correspondingly, the value of the isodose curve through the center of the beam on the surface of object 13 equals Dmax=100%. Thus, by using a wedge function instead of a wedge-shaped absorber an efficiency factor of "1" or 100% can be established; in other words, the dose delivered at that point is 100% of the prescribed dose, although the same relative isodose profiles are maintained. That means that the therapist does not have to take into account a wedge factor when defining the treatment, although wedge shaped isodose curves are established.

FIG. 2 shows those portions of treatment unit 100 which are necessary to carry out the invention. Treatment unit 100 comprises central processing unit 18 which is programmed by the therapist according to the instructions of the oncologist, so that the radiation treatment device carries out the prescribed radiation treatment. Through keyboard 19, the prescribed delivery of the radiation treatment is input.

Central processing unit 18 is connected, on the one hand, with the input device, such as keyboard 19, for inputting the prescribed delivery of the radiation treatment and, on the other hand, with a dose control unit 61 that generates the desired values of radiation for the controlling trigger system 3. Trigger system 3 then adapts the pulse repetition frequency or other parameters in a corresponding, conventional manner. The ability to change the radiation output is generally known and it is particularly advantageous to use a digital dosimetry system because then it can easily be controlled by the digital output of central processing unit 18.

Central processing unit 18 includes control unit 76 which controls the execution of the program and which supplies position signals P for controlling the opening of plate arrangement 4 and nominal dose signals D (corresponding to the plate position that would be demanded using prior art methods, that is, without regard to output factor compensation) for adjusting the radiation output at the output of radiation source 17. A memory 77 is also provided in or is connected to the central processing unit 18 for supplying correction signals C, which the processing unit uses to adjust the radiation output dependent on the position signals P supplied from position sensors 44 and 45 to achieve the predetermined constant output factor.

The preferred arrangement of the memory unit is that, for each plate position (field size), it has stored a corresponding wedge correction signal C. The memory thus stores a table of wedge correction factors. If more than one set of movable plates is included in the system, then the table will be correspondingly multi-dimensional and arranged using any known data structure, so that a wedge correction factor is available for any combination of plate positions.

Control unit 76 and memory 77 apply the nominal dose and wedge correction signals D and C, respectively, to a combination circuit 78, which combines the values to generate set signals S. The set signals S are in turn applied to the dose control unit 61, which sets the radiation output.

The combination circuit 78 will depend on the form in which the wedge correction signals are generated and stored. Assume that the wedge correction signals C are stored as additive offsets to the set radiation output. In this case, the combination circuit will be an adder which adds the wedge correction signals C to nominal dose signals D. This is the preferred embodiment, since it is simplest. If, however, the wedge correction factors are multipliers, for example, an increase in radiation output from a sensed value of 72% would require a multiplicative correction signal of about 139%. Instead of storing actual values of the wedge correction signals C, it is also possible to store the parameters of a wedge correction function for the various field sizes. The processing unit would then evaluate the wedge correction function for each current field size using the parameters stored in the memory, and would then generate the wedge correction signals (additive or multiplicative) itself. Wedge correction signals C, wedge correction factors and wedge correction functions can be referred to collectively as wedge corrections.

The wedge correction signals are determined before actual treatment of a patient in one or more calibration runs. To determine relative wedge correction values, a reference surface is irradiated with a known reference plate position, and the radiation output over the surface is sensed by a conventional sensing device, which generates radiation output signals. These output signals are then applied to processing unit 18. In particular, the radiation output at a reference point (e.g., at the center of the beam) is sensed. The reference surface need not lie in the patient plane, although if it does, the calibration will typically be easier and more accurate.

The plates are then moved to a new opening position, the radiation output is sensed and the needed amount of adjustment is determined to create the proper isodose profile for that position. This process is continued until correction values are stored for the reference surface over the entire range of motion of the plates. If more than one set of movable plates is included, then correction values will be sensed and stored for each combination of plate positions; the number of combinations will depend on the desired or required resolution.

The correction values indicate by how much the radiation output (for example, dose rate) is to be changed (via the wedge correction signals) such that the delivered dose distribution is equal to the desired dose distribution, that is, the isodose profiles are generated corresponding to what they would be if the radiation output were held constant and a physical wedge were included in the beam path. During actual treatment, for each plate position, the processing unit adjusts the radiation output to correspond to what is needed to generate the correct isodose profile. Since no actual physical wedge is included, however, and the system is calibrated for 100% output at the reference point, the therapist need not perform any calculations to adjust for a wedge factor. If additive offsets are chosen for the wedge correction factors, then the difference between the sensed output values and the desired output value is stored. If multiplicative correction factors are chosen, then ratios are stored. Alternatively, any known function approximation method may be used to generate the parameters of an approximating function of the additive or multiplicative wedge correction factors required.

A "course" of radiation treatment may, and often does, have more than one field, and may run over several different sessions. In some cases, hundreds of different (and, in some cases, fixed) sequential fields with different wedges are used during a course, for example, to provide proper irradiation of a field that has a complicated geometry or prescribed dose profile, to lessen discomfort to the patient, or to adjust the field as a tumor shrinks during treatment. The invention therefore also comprises an optional verification and recording or "auto set-up" system 102 (see FIG. 2), which stores and downloads to the radiation system (via the CPU 18 or directly into the memory) the parameters, for example, of the geometry, of the various fields of the course of treatment, and/or the tables of wedge correction factors that were derived during earlier calibration runs for the various fields.

Figure 5:
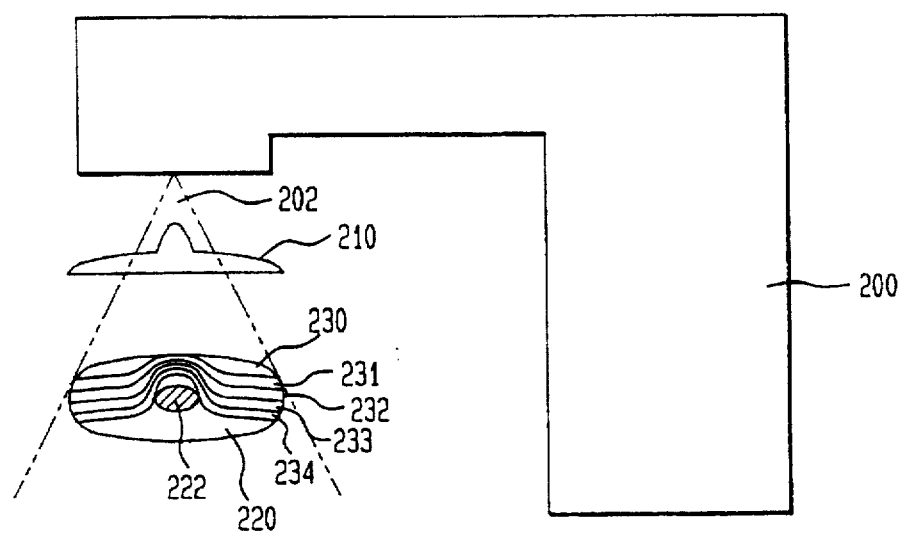
FIG. 5 shows a radiation distribution dose resulting from a custom compensator.

In a second embodiment of the present invention, a compensator (also known as a compensating tilted is simulated. A custom compensator assists in delivering radiation to the shape of a field to be treated when the field has complicated geometry. As set forth above, radiation is distributed through a field at different doses (e.g., see FIG. 3). FIG. 5 shows a radiation distribution dose resulting from a custom compensator. Gantry 200 provides radiation beam 202 through custom compensator 210 to object 220. Spinal cord 222 is located in object 220. Due to the nature of the spinal cord, it is desirable to remove spinal cord 222 from the field to be treated. As set forth above, a radiation beam incident on an irregular or sloping surface produces skewing of the isodose/radiation curves. In this example, compensator 210 absorbs the radiation such that spinal cord 222 is not treated with radiation. Radiation dose curves 230-234 show how the field is treated without exposing spinal cord 222 to radiation. Thus, when a compensator is used, the dose distribution can be controlled to accurately match the field to be treated while avoiding areas which should not be exposed to radiation.

When custom compensators are used, a new compensator is made for each patient. For example, metal can be poured into a milled mold, or square blocks (e.g., 1 cm×1 cm) can be stacked and taped together to create the metal compensator. The custom compensator is also changed for each patient. Usually, the metal compensator hangs on the block tray of the accelerator in the third accessory slot. The third accessory slot is the slot closest to the patient and usually 15 to 20 cm from the patient's skin. Compensators are set forth in greater detail in Faiz M. Khan, "The Physics of Radiation Therapy," Williams & Wilkins, 1994, pages 300–307, which is incorporated by reference for all purposes.

Figure 6:
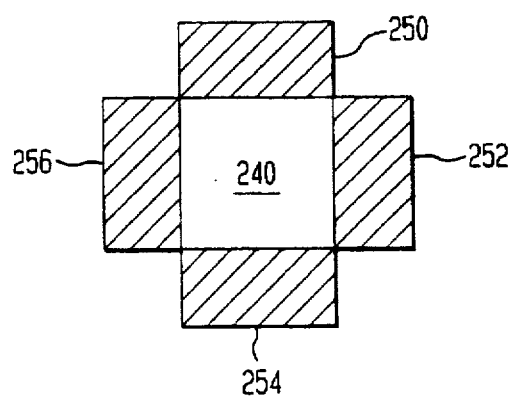
FIG. 6 illustrates how the size of the radiation beam can be delimited by jaws.

FIG. 6 illustrates how the size of the radiation beam can be delimited by jaws. Before reaching the metal compensator, the radiation beam passes through area 240 which is defined by jaws 250, 252, 254, 256. These jaws 250, 252, 254, 256 are similar to plates 4 in FIG. 1 such that they are substantially impervious to the emitted radiation. These jaws 250, 252, 254, 256 delimit the beam to a predetermined rectangular shape. The beam is then passed through the metal compensator before being used to treat the object with radiation. Additionally, a multi-leaf collimator can be used with jaws 250, 252, 254, 256. When a collimator is used, the leaves within the collimator are positioned such that they delimit the radiation beam to produce a pattern which closely matches the parameters of the field on the object to be irradiated. The collimator can also be rotated to match the parameters of the field better. Whether jaws and/or a multi-leaf collimator is used, the delimited beam is passed through a compensator before reaching the patient.

Figure 7:
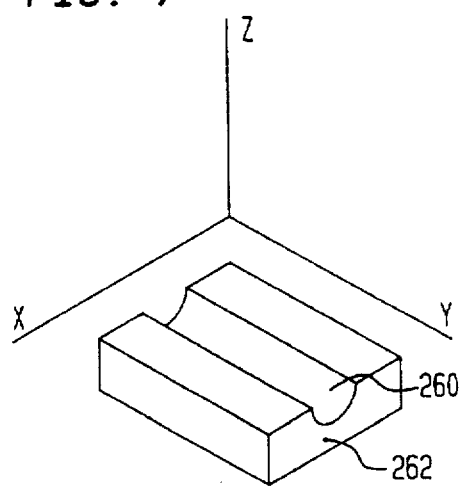
FIG. 7 illustrates an example of a desired radiation pattern on the patient plane.

FIG. 7 illustrates an example of a desired radiation pattern on the patient plane. In this example, the spinal cord has been avoided as shown by area 260 which was not treated with radiation 262. Therefore, after the radiation beam was delimited to a rectangle by jaws 250, 252, 254, 256, a compensator absorbed radiation in the radiation beam such that the spinal cord was not treated with radiation. In the second embodiment of the present invention, the three-dimensional radiation dose shown in FIG. 7 is obtained without a compensator. This is done by first dividing the field to be treated into sections and then using wedge corrections (as described above in the first embodiment) for each section. If wedge corrective signals are used, they can be either additive offsets or multipliers.

Figure 8:
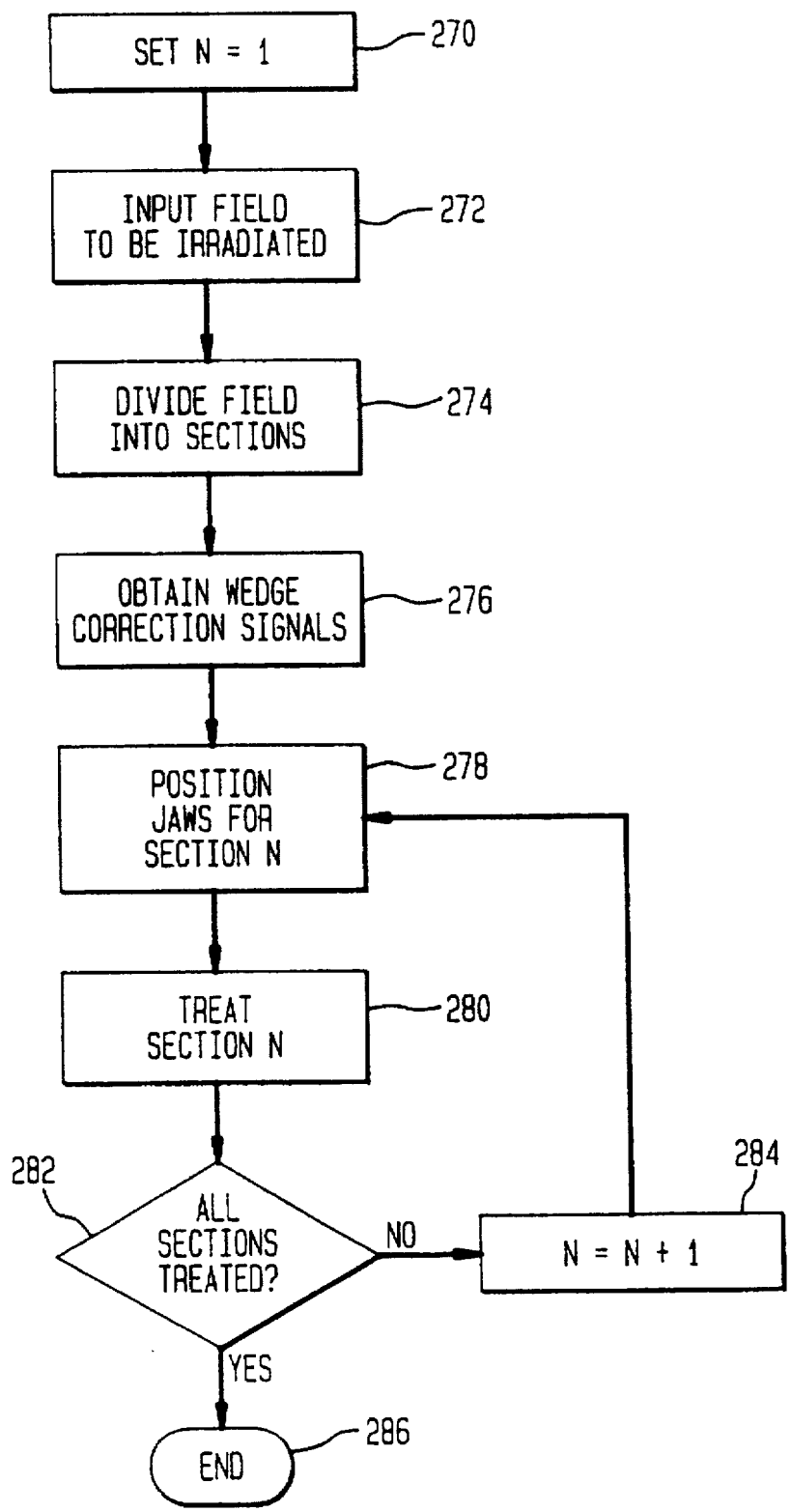
FIG. 8 is a process flowchart for obtaining a desired radiation pattern without a compensator.

FIG. 8 is a process flowchart for obtaining a desired radiation pattern without a compensator. An extensive software program is used to obtain the desired radiation pattern. At step 270, N is set equal to 1. At step 272, the field to be irradiated is inputted into the system's control unit. This can be done through an input device such as keyboard 19 in FIG. 1. The system's control unit could be control unit 76 of treatment unit 100 in FIG. 1. At step 274, the software program calculates an efficient way to divide the inputted field up into separate sections. Smaller sections are located near the edge of the field and near areas which should avoid radiation (e.g., the spinal cord). These smaller sections provide for more accurate radiation exposure in these important areas.

At step 276, wedge corrections (see description in first embodiment for more details) are obtained for each of the separate sections. At step 278, the jaws are positioned over section N (N being the first section). At step 280, the wedge corrections are used, and the jaws and the radiation dose are controlled during the treatment of section N. In the preferred embodiment, the radiation dose is defined at the isocenter of the section to be treated. For more control, the radiation source in gantry 6 can be rotated (as shown in FIG. 1). When the radiation source is rotated, the rotation occurs when the jaws are being set-up for treatment; rotation of the source does not occur during radiation treatment. Radiation treatment is described in greater detail above in the first embodiment. At step 282, the software program checks whether all the sections have been treated. If all the sections have not been treated, the program moves to step 284 and performs the calculation N=N+1. The program then returns to step 278 and positions the jaws for section N (N being the second section this time). At step 280, this section N is treated with radiation. This continues until all the sections are treated, and the program ends at step 286.

Figure 9:
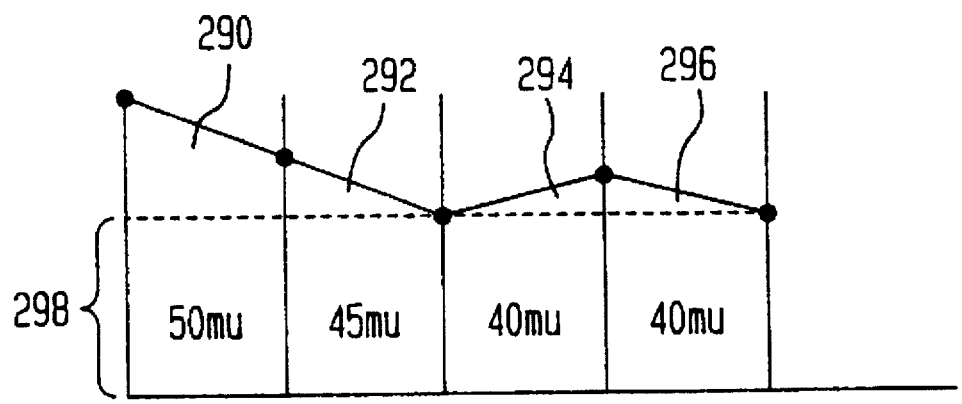
FIG. 9 illustrates a two-dimensional view of a field to be irradiated which includes four sections.

FIG. 9 illustrates a two-dimensional view of a field to be irradiated which includes four sections. Sections 290, 292, 294, 296 comprise different monitor units, 50 mu, 45 mu, 40 mu and 40 mu, respectively. Monitor units are determined from the internal calibration of the linear accelerator. As set forth above in the first embodiment, the jaws (or plates) can move at a constant speed and the radiation dose rate can be varied to provide the required monitor units and to obtain the desired wedge effect. In a first arrangement, sections 290, 292, 294 and 296 are all treated as four separate sections. Each of these sections has a corresponding wedge correction signal and/or a corresponding wedge correction function. These values can be calculated, or they can be extracted from a table based on the dimensions of the particular section. In a second arrangement, bottom section 298 of sections 290, 292, 294, 296 is treated with radiation as a first section or layer, and then the top areas of sections 290, 292, 294, 296 are each treated as a separate section (total of five sections). In this arrangement, the largest possible square block in the field is treated first and then the remaining area is divided into sections for separate treatment with independent wedge functions. Therefore, layers and sections can be used to treat an unusually shaped field. This second arrangement can speed up the treatment sessions.

In another arrangement of the second embodiment, in addition to the metal compensator, the multi-leaf collimator is also simulated with the extensive software of the present invention. The multi-leaf collimator is simulated by dividing the field to be treated up into smaller sections. Therefore, the radiation pattern matches the shape of the field without a multi-leaf collimator.

Figure 10:
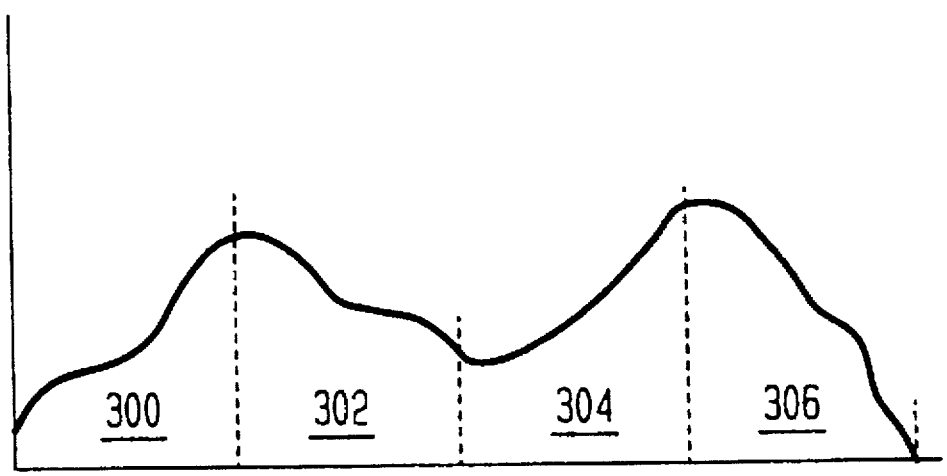
FIG. 10 illustrates a two-dimensional example of a field which can be effectively treated using arbitrary monotonic functions.

In another embodiment of the present invention, a variable radiation dose rate is utilized along with a constant jaw speed to create arbitrary monotonic functions. FIG. 10 illustrates a two-dimensional example of a field which can be effectively treated using arbitrary monotonic functions. In this example, the field is broken up into 1 inch wide strips 300, 302, 304 and 306. Each strip 300, 302, 304 and 306 is then individually treated with radiation. By varying the radiation dose rate, unusually shaped strips can be obtained. Therefore, strips 300, 302, 304 and 306 can be effectively treated even though they are not wedge shaped. To treat these unusually shaped strips, complex calculations are performed by a software program. The calculations are used for determining the desired movement of the jaw (or plates in a collimator) and the desired variations in radiation dose rate.

The software program begins by calculating the dose rate as a function of position:

$$mu(x) = \int \frac{dmu(x)}{dt} dt$$

mu(x) is the number of monitor units to be delivered to a point in the field. The position of this point in the field is called x. This position is restricted to one dimension (i.e., the dimension along which the collimator or jaw is moved at a constant velocity $v_j$). mu(x) is not normally described in functional terms (i.e., closed analytic form). Instead, mu(x) is usually described as a set of discrete values $\{mu(x_i)$, where $x_i$ is the position of the $i^{th}$ point in the field$\}$ over the length of the field $\{e.g., mu(1)=5, mu(2)=4, mu(3)=3, mu(4)=2\}$. mu(x) can be represented in terms of $v_j$ and the time derivative of mu(t), which is dose rate as a function of the time $t_1$ during which the collimator/jaw is in motion. To determine $v_j$ and the time derivative of mu(t), the following is used:

$$mu(x) = mu_{idle} + mu_j(x)$$

$mu_{idle}$ is the number of monitor units that every point will receive when the jaw is stationary and the field is fully exposed. $mu_j(x)$ is the number of monitor units that point x receives during jaw motion. The dose rate for $mu_j(x)$ is the maximum available dose rate. The dose rate for $mu_j(x)$ is described by the following:

$$mu_j(x) = \int_{(x - x_s)/v_j}^{(x_f - x_s)/v_j} [\text{time derivative of } mu(t)] \, dt$$

where the limits of the integral represent the total time that point x was exposed to radiation while the jaw was moving. $x_s$ is the position of the stationary jaw, and $x_f$ is the final position of the moving jaw. The stationary jaw edge is parallel to the moving jaw edge. The time derivative of mu(t) can be described as the following polynomial:
time derivative $$mu(t) = \sum_{N=0}^{N} a_n t^n$$

and the integral is done to product a theoretical polynomial representation or $mu_j(x)$ in the following manner:

$$mu_j(x) = \sum_{N=0}^{N} a_n/(n+1) \left( \left[ \frac{X_f + X_s}{V_j} \right]^{n+1} - \left[ \frac{X - X_s}{V_j} \right]^{n+1} \right)$$

With these equations, one can find the set of polynomial coefficients $a_n$ and velocity $v_j$ which can be used to reproduce the whole set of $mu(x_i)$ values. This can be done by a linear regression technique where the data values of $mu(x_i)$ (e.g., $\{mu(1)=5, mu(2)=4, mu(3)=3, mu(4)=2\}$) are filled to the theoretical polynomial representation of mu(x). Linear regression is a known technique for determining coefficients. Other filling techniques can also be used. For example, "Numerical Recipes In C," by Vetterling, Press, Flannery and Teukolsky, 1992, Cambridge University Press, describes various fitting techniques. The number of coefficients N should be equal to the number of data points in the set of $mu(x_i)$. In the example $\{mu(1)=5, mu(2)=4, mu(3)=3, mu(4)=2\}$, N=4. Once the coefficients an are known, the time derivative of mu(t) is fully described, and the required dose rate (as a function of time during which the jaw moves) and the velocity of the jaw are obtained.

We claim:

1. A method for adjusting radiation output delivered to an object from a radiation source, comprising the following steps:
- defining a field on the object for irradiation;
- generating a radiation beam having a variable radiation output and a substantially lossless beam path from a radiation source to the object;
- dividing the field into multiple sections, each of the multiple sections having defined parameters;
- calculating wedge corrections for each of the multiple sections;
- defining an opening between the radiation source and the object, the opening being placed over one of the sections, the opening capable of delimiting the radiation beam to the defined parameters of the section; and
- using the wedge corrections to treat each of the sections with radiation.

2. The method for adjusting radiation output delivered to an object from a radiation source of claim 1, further comprising the step of varying the radiation output from the radiation beam.

3. The method for adjusting radiation output delivered to an object from a radiation source of claim 1, wherein the opening is defined by at least one jaw, the jaw being capable of blocking radiation from the radiation source.

4. The method for adjusting radiation output delivered to an object from a radiation source of claim 1, further comprising the step of rotating the radiation source to change the position of the radiation beam.

5. The method for adjusting radiation output delivered to an object from a radiation source of claim 1, further comprising the step of storing the wedge corrections in a memory.

6. The method for adjusting radiation output delivered to an object from a radiation source of claim 1, whereby a custom compensator is simulated.

7. The method for adjusting radiation output delivered to an object from a radiation source of claim 1, wherein the opening is defined by a multi-leaf collimator, the multi-leaf collimator being capable of blocking radiation from the radiation source.

8. The method for adjusting radiation output delivered to an object from a radiation source of claim 1, wherein the wedge corrections include at least one of a wedge corrective signal, a wedge correction factor and a wedge correction function.

9. The method for adjusting radiation output delivered to an object from a radiation source of claim 1, wherein the wedge corrections obtain values from a table, the values from the table being based on the defined parameters of the sections.

10. A method for adjusting radiation output delivered to an object from a radiation source, the radiation source being capable of generating a radiation beam, the radiation beam having variable radiation output, the method comprising the steps of:
- inputting parameters of a field on the object for irradiation;
- calculating an efficient way to divide the inputted field into multiple sections, the multiple sections having defined parameters;
- obtaining wedge corrections;
- positioning an opening over one of the sections, the opening being between the radiation source and the object, and the opening being capable of delimiting the radiation beam to the defined parameters of each of the sections;
- using the wedge corrections to treat each of the multiple sections with radiation.

11. The method for adjusting radiation output delivered to an object from a radiation source of claim 10, further comprising the step of defining radiation dose at the isocenter of each of the sections.

12. The method for adjusting radiation output delivered to an object from a radiation source of claim 10, further comprising the step of rotating the radiation source to change the position of the radiation beam.

13. The method for adjusting radiation output delivered to an object from a radiation source of claim 10, wherein the opening is defined by at least one jaw, the jaw being capable of blocking radiation from the radiation source.

14. A system for adjusting radiation output delivered to a field to be irradiated on an object, comprising:
- a radiation source for generating a radiation beam, the radiation beam having a variable radiation output;
- beam-shielding means for delimiting the output radiation beam to predetermined parameters;
- a dose controller for varying an amount of the radiation output from the radiation source; and
- processing means for dividing the field to be irradiated into multiple sections, each of the sections having defined parameters, and for calculating at least one of wedge corrections and monotonic functions for each of the multiple sections.

15. The system for adjusting radiation output delivered to a field to be irradiated on an object of claim 14, wherein the wedge corrections are used to treat each of the multiple sections with radiation.

16. The system for adjusting radiation output delivered to a field to be irradiated on an object of claim 14, further comprising a position controller for varying the rotational position of the radiation source.

17. The system for adjusting radiation output delivered to a field to be irradiated on an object of claim 15, further comprising a memory for storing the wedge corrections.

18. The system for adjusting radiation output delivered to a field to be irradiated on an object of claim 14, wherein the beam-shielding means are jaws.

19. The system for adjusting radiation output delivered to a field to be irradiated on an object of claim 15, wherein the wedge corrections include at least one of a wedge corrective signal, a wedge correction factor and a wedge correction function.

20. The system for adjusting radiation output delivered to a field to be irradiated on an object of claim 15, wherein the wedge corrections obtain values from a table, the values from the table being based on the defined parameters of the sections.

21. The system for adjusting radiation output delivered to a field to be irradiated on an object of claim 14, wherein the beam-shielding means is a multi-leaf collimator.

22. Method for adjusting radiation output delivered to an object from a radiation source, comprising the following steps:
- defining a field on the object for irradiation;
- generating a radiation beam having a variable radiation output and a substantially lossless beam path from a radiation source to the object;
- dividing the field into multiple sections, each of the multiple sections having defined parameters;

calculating monotonic functions for each of the multiple sections;

defining an opening between the radiation source and the object, the opening being placed over one of the sections, the opening capable of delimiting the radiation beam to the defined parameters of the section;

varying the radiation output from the radiation beam; and using the monotonic functions to treat each of the sections with radiation.

23. The method for adjusting radiation output delivered to an object from a radiation source of claim 22, wherein the opening is defined by at least one jaw, the jaw being capable of blocking radiation from the radiation source.

24. The method for adjusting radiation output delivered to an object from a radiation source of claim 22, whereby a custom compensator is simulated.

25. The method for adjusting radiation output delivered to an object from a radiation source of claim 22, wherein the opening is defined by a multi-leaf collimator, the multi-leaf collimator being capable of blocking radiation from the radiation source.

* * * * *